US007964587B2

(12) United States Patent
Ames et al.

(10) Patent No.: US 7,964,587 B2
(45) Date of Patent: Jun. 21, 2011

(54) TOCOPHEROL AND TOCOTRIENOL AEROSOLS

(75) Inventors: Bruce N. Ames, Berkeley, CA (US); Qing Jiang, Berkeley, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 1113 days.

(21) Appl. No.: 11/159,917

(22) Filed: Jun. 22, 2005

(65) Prior Publication Data

US 2005/0239876 A1 Oct. 27, 2005

Related U.S. Application Data

(63) Continuation of application No. 10/301,211, filed on Nov. 21, 2002, now abandoned.

(51) Int. Cl.
*A61K 31/355* (2006.01)
*A01N 43/16* (2006.01)

(52) U.S. Cl. ........................................ 514/183; 514/458

(58) Field of Classification Search .................. 514/458, 514/560
See application file for complete search history.

(56) References Cited

U.S. PATENT DOCUMENTS

| | | | | |
|---|---|---|---|---|
| 5,919,827 | A * | 7/1999 | Barberich et al. | 514/651 |
| 6,242,479 | B1 * | 6/2001 | Wechter | 514/456 |
| 6,410,589 | B2 | 6/2002 | Wechter | |
| 6,571,791 | B2 * | 6/2003 | Scheuch et al. | 128/200.22 |
| 6,902,739 | B2 * | 6/2005 | McPeak et al. | 424/442 |
| 7,074,825 | B2 * | 7/2006 | Mo et al. | 514/456 |
| 2002/0032171 | A1 | 3/2002 | Chen et al. | |
| 2003/0007961 | A1 | 1/2003 | Wilburn | |
| 2003/0013693 | A1 | 1/2003 | Guivarc'h et al. | |
| 2003/0100603 | A1 | 5/2003 | Beinlich et al. | |
| 2003/0118672 | A1 | 6/2003 | McPeak et al. | |
| 2003/0144219 | A1 | 7/2003 | Phinney et al. | |
| 2003/0236301 | A1 | 12/2003 | Sanders et al. | |

FOREIGN PATENT DOCUMENTS

| | | |
|---|---|---|
| JP | 6256181 | * 9/1994 |
| WO | WO 00/59492 | * 10/2000 |

OTHER PUBLICATIONS

Moyad et al. Vitamin E, alpha and gamma tocopherol and prostate cancer. Seminars in Urologic Oncology, vol. 17, No. 2, May 1999, pp. 85-90.*
Wood et al. Pharmacologic Treatment of Cancer Pain. Review Article. 1996.*
Gillenwater et al. Adutl and Pediatric Urology. Fourth Edition, vol. one. 2002. p. 597.*
Definition of inhibition. www.freedicitonary.com 2009.*
Defiinition of prohibiting. www.freedicitionary.com. 2009.*
Science Daily, 2008.*
New York Times, 2009.*
Translation of JP 06256181. 1993.*
Definition of inhibition. www.freedictionary.com. 2009.*
Definition of prohibiting. www.freedictionary.com. 2009.*
Science Daily, http://www.sciencedaily.com/releases/2008/12/081210131046.htm. 2008.*
New York Times, http://www.nytimes.com/2009/03/24/health/24brod.html. 2009.*
Trnaslation of JP06256181. 1993.*
Inturrisi et al. Management of Cancer Pain: Pharmacology and Principles of Management. Cancer, 63: 2308-2320, 1989.*
Christen et al., Gamma-Tocopherol traps mutagenic electrophiles such as NOx and complements alpha-tocopherol, Proc. Natl Acad. Sci. vol. 94 No. 7 pp. 3217-3222 Apr. 1997.
Granstrom, What's Wrong With Vitamin E?, Life Extension Magazine, May 2002.
Gysin et al, Gamma-Tocopherol inhibits human cancer cell cycle progressioin and cell proliferation by down-regulation of cyclins, FASEB J. (Oct. 4, 2002) 10.1096/fj.02-0362.
McIntyre et al, Antiproliferative and Apoptotic Effects of Tocopherols and Tocotrienols on Preneoplastic and Neoplastic . . . , Proc Soc Exp Biol Med. Sep. 2000;224(4):292-301.

* cited by examiner

*Primary Examiner* — Brandon J Fetterolf
*Assistant Examiner* — Anna Pagonakis
(74) *Attorney, Agent, or Firm* — Richard Aron Osman

(57) ABSTRACT

Anti-inflammatory compositions include medicaments comprising predetermined amounts of a phytyl substituted chromanol and a prostaglandin $E_2$ inhibitor, wherein: said medicament is in unit dosage form suitable for pharmaceutical administration; said phytyl substituted chromanol is a gamma-tocopherol, delta-tocopherol, gamma-tocotrienol or delta-tocotrienol; said $PGE_2$ inhibitor is a non-steroidal anti-inflammatory drug or an omega-3 fatty acid, such as docosahexaenoic acid and eicosapentaenoic acid.

6 Claims, No Drawings

TOCOPHEROL AND TOCOTRIENOL AEROSOLS

This application is a continuation of prior application Ser. No. 10/301,211 filed Nov. 21, 2002 now abandoned.

This invention was made with US Government support under National Institute of Environmental Sciences Center Grand ES01896. The Government has certain rights in this invention.

FIELD OF THE INVENTION

The field of the invention is the use of tocopherols and tocotrienols in anti-inflammatory medicaments.

BACKGROUND OF THE INVENTION

Inflammatory diseases such as rheumatoid arthritis, asthma and hepatitis are among the leading causes of death and disability in the world. Chronic inflammation contributes to the development of degenerative diseases including cancer (1), cardiovascular diseases (2) and neuro-degenerative disorders (3). During inflammation, various eicosanoids derived from arachidonic acid (AA) play a key role in mediating inflammatory response (4). For instance, prostaglandin $E_2$ ($PGE_2$), which is synthesized from cyclooxygenase (COX)-catalyzed oxidation of AA, is believed to cause pain and fever (4, 5), as well as activate cytokine formation (6). $PGE_2$ can be produced by either the constitutive form (COX-1) or the inducible form (COX-2) of cyclooxygenase (7). In most inflammatory conditions, COX-2 is up-regulated and is the primary enzyme responsible for the formation of pro-inflammatory $PGE_2$ (7). Leukotriene $B_4$ ($LTB_4$), another oxidized product derived from AA through the 5-lipoxygenase-catalyzed pathway, is one of the most potent chemotactic agents (8). Because of the central roles of $PGE_2$ and $LTB_4$, COX-2 and 5-lipoxygenase have been recognized as key targets for the drug therapy in inflammation-associated diseases. In particular, COX-2 inhibitors, which are classified as non-steriod anti-inflammatory drugs (NSAIDs), have been proven to be effective in attenuating inflammatory response and beneficial for certain inflammation-associated diseases (9).

Vitamin E consists of eight compounds; four tocopherols (alpha-, beta-, gamma-, and delta-) and four tocotrienols (alpha-, beta-, gamma-, and delta-). Among them, only alpha-tocopherol has been extensively studied. Gamma-tocopherol (gamma-T) is the major form of vitamin E in the US diet. However, it has drawn little attention compared with alpha-tocopherol, the primary form of vitamin E found in most supplements. Delta-tocopherol (delta-T) is another form of vitamin E that is rich in some food sources (often found with gamma-tocopherol, e.g. in soybeans and soybean oil). Tocotrienols are mainly abundant in palm oil.

We recently found that gamma-tocopherol (gamma-T), and its physiological metabolite, 2,7,8-trimethyl-2-(b-carboxyethyl)-6-hydroxychroman (gamma-CEHC), inhibits COX-2-catalyzed formation of $PGE_2$, as assayed in lipopolysaccharide-stimulated macrophage and interlukin-1b activated epithelial cells (10; see also our review, 18). This indicates that gamma-T and its metabolite may have anti-inflammatory properties that are similar to those of NSAIDs. In contrast, alpha-tocopherol (alpha-T), the predominant form of vitamin E in the tissues and most supplements, is much less effective in this regard (10). It was not clear, however, whether gamma-tocopherol would reach significant levels in tissues to exert significant effects in vivo.

Here we show that this bioactivity of gamma-T is demonstrable in vivo, and more importantly, establish that there are three pathways by which gamma-T inhibits inflammation, and indicates that gamma-T has superior and supplemental pharmaceutical potential over the commonly used cyclooxygenase inhibitors. We disclose the use of gamma-T, delta-T, and their corresponding metabolites (gamma-CEHC, Delta-CEHC), as well as combinations of gamma-T and delta-T, and these tocopherols with gamma-tocotrienol or delta-tocotrienol, in the form of supplements or drugs, particularly in combination with existing drugs such as NSAIDs to treat inflammation, particularly inflammatory diseases such as arthritis, bowel diseases, and asthma. These subject medicaments can also be used to treat and prevent chronic diseases associated with inflammation such as cancer and cardiovascular disorders.

U.S. Pat. Nos. 6,204,290; 6,242,479; 6,410,589; and 6,239,171 appear relevant to this disclosure.

SUMMARY OF THE INVENTION

The invention provides methods and compositions for inhibiting inflammation. The compositions include medicaments comprising predetermined amounts of a phytyl substituted chromanol and an inhibitor of prostaglandin $E_2$ ($PGE_2$) formation, wherein: said medicament is in unit dosage form suitable for pharmaceutical administration; said phytyl substituted chromanol is selected from the group consisting of gamma-tocopherol, delta-tocopherol, gamma-tocotrienol and delta-tocotrienol; and said $PGE_2$ inhibitor is selected from the group consisting of an omega-3 fatty acid cyclooxygenase substrate and a non-steroidal anti-inflammatory drug (NSAID) cyclooxygenase inhibitor.

The phytyl-substituted chromanol is typically isolated or purified to homogeneity or near homogeneity. In particular embodiments, the medicament comprises less alpha-tocopherol than is present in natural Vitamin E compositions, preferably less than 5% alpha-tocopherol, more preferably less than 0.5%, more preferably less than 0.05%. The medicament may comprise various mixtures of gamma- and delta-tocopherol and gamma and delta-tocotrienol.

Exploiting the synergy of the components of the medicaments, the $PGE_2$ inhibitor may be provided at a dosage that is suboptimally therapeutic, or to various degrees, subtherapeutic, when administered alone. In particular embodiments, the $PGE_2$ inhibitor is an NSAID cyclooxygenase inhibitor of Table 1; and/or a cyclooxygenase-2 (COX) selective inhibitor. In other embodiments, the $PGE_2$ inhibitor is an omega fatty acid cyclooxygenase substrate, such as docosahexaenoic acid (DHA) or eicosapentaenoic acid (EPA).

The invention also provides methods of inhibiting inflammation by administering to a patient a subject medicament.

DETAILED DESCRIPTION OF PARTICULAR EMBODIMENTS OF THE INVENTION

We disclose that gamma-T, unlike alpha-T which has no activity in our studies, can be used as a drug to treat or prevent inflammatory diseases. We have shown in an animal model of inflammation, which mimics joint diseases such as arthritis and other inflammatory diseases, that gamma-T inhibits inflammation by blocking three pathways: pro-inflammatory prostaglandin $E_2$ ($PGE_2$), leukotriene $B_4$ ($LTB_4$), and TNF-alpha. $PGE_2$ is known to mediate inflammatory responses, including pain and fever, as well as cytokine formation; $LTB_4$ is one of the most potent chemotactic agents; and TNF-alpha is a key cytokine that regulates inflammatory response. Because most commonly used non-steroid anti-inflammatory drugs (NSAIDs), such as cyclooxygenase inhibitors, only inhibit cyclooxygenase-catalyzed $PGE_2$, the inhibition of $PGE_2$, $LTB_4$ and TNF-alpha indicates that tocopherols (including gamma-T) have superior and supplemental pharmaceutical values over commonly used anti-inflammatory drugs.

Combinations of gamma-T, delta-T or gamma-tocotrienol and delta-tocotrienol are superior to the use of just one of these compounds because each compound exhibits distinct activities against $PGE_2$, $LTB_4$, and TNF-alpha and distinct bio-distribution. Although tocopherols in the vitamin E family differ only in one or two methyl groups, their relative bioactivities are not predictable simply based on the number of methyl groups. For instance, while alpha-T, beta-tocopherol (beta-T), and alpha-tocotrienol showed weak to no inhibitory effect on $PGE_2$ (e.g. ref. 10); gamma-T, delta-T, and gamma-tocotrienol effectively inhibit $PGE_2$, with the apparent IC50s of 5-10 µM (gamma-T), 2.5-5 µM (delta-T), and 1-2.5 µM (gamma-tocotrienol). Our data indicate that delta-T and gamma-tocotrienol are better cyclooxygenase inhibitors than gamma-T in some systems. In addition, the relative distribution of gamma-T, delta-T and gamma-tocotrienol in the body is different due to the differential transport and metabolism of these compounds. For instance, upon supplementation with vitamin E, tocotrienols are more likely to be found in the skin and adipose tissue, whereas gamma-T and delta-T levels are elevated in the skin, muscle, adipose, heart and other tissues. Delta-T also appears to be retained in the body for a shorter time than gamma-T. Hence, a combination of delta-T and gamma-T provides better therapeutic effects, as delta-T is more potent against $PGE_2$, while the effects of gamma-T can last longer. Similarly, a combination of gamma-tocotrienol and gamma-T is superior for treating certain inflammatory conditions, such as inflammatory skin (dermal) diseases.

Combinations of tocopherols (e.g. gamma-T and delta-T), and tocotrienols (e.g. gamma-tocotrienol and delta-tocotrienol) with other anti-inflammatory drugs, such as cyclooxygenase inhibitors, provide enhanced therapeutic effects, compared with the use of these drugs alone. Some of the NSAIDs are much more potent inhibitors of $PGE_2$ than gamma-T. Though gamma-T is considered to be a moderate inhibitor of $PGE_2$, it has additional inhibitory activity on $LTB_4$, lipid peroxidation, and TNF-alpha. A combination of gamma-T with other NSAIDs improves therapeutic effects and lowers the required dose of NSAIDs, thereby reducing such side effects as ulcerogenesis.

Combinations of tocopherols and tocotrienols with dietary supplementation of omega-3 fatty acid also provide additive or synergistic anti-inflammatory effects. Omega-3 fatty acids, including docosahexaenoic acid (DHA) and eicosapentaenoic acid (EPA), have mild anti-inflammatory activity by way of lowering arachidonic acid, the substrate of cyclooxygenase and lipoxygenase for the generation of $PGE_2$ and $LTB_4$. Because tocopherols and tocotrienols inhibit cyclooxygenase- and lipooxygenase-catalyzed synthesis of $PGE_2$ and $LTB_4$, combinations of tocopherols (or tocotrienols) with dietary supplementation of DHA or EPA results in a more potent decrease in the pro-inflammatory $PGE_2$ and $LTB_4$, and thus provide stronger anti-inflammatory effects than either of them alone.

Gamma-T, delta-T, gamma-tocotrienol, or their combinations are also useful in cancer prevention or therapy. COX-2 and $PGE_2$ are elevated in inflammation-associated diseases, including cancer, and frequent intake of non-steroid anti-inflammation drugs, such as aspirin, reduce the risk of certain cancers. In addition to the cyclooxygenase-related mechanism, the lipoxygenase-relative pathways (one of the products of 5-lipoxygenase is leukotriene $B_4$), also contributes to the development of certain cancers. We confirmed that gamma-T showed anti-proliferative effects on human prostate epithelial cancer cells and lung epithelial cancer cells by mechanisms associated with the inhibition of both cyclooxygenase and lipoxygenase catalyzed reactions. The anti-inflammatory effects of gamma-T are also beneficial in preventing or treating cardiovascular disease, another inflammation-associated disorder.

Accordingly, the invention provides methods and compositions for inhibiting or reducing inflammation or any manifestation thereof, and/or for reducing the likelihood of developing or for promoting a resistance to inflammation or any manifestation thereof. The compositions include medicaments comprising predetermined amounts of a phytyl-substituted chromanol and an inhibitor of prostaglandin $E_2$ ($PGE_2$) formation, wherein said $PGE_2$ inhibitor is selected from the group consisting of an omega-3 fatty acid cyclooxygenase substrate and a non-steroidal anti-inflammatory drug (NSAID) cyclooxygenase inhibitor. In preferred embodiments, said medicament is in unit dosage form suitable for pharmaceutical administration; and/or said phytyl-substituted chromanol is selected from the group consisting of gamma-tocopherol, delta-tocopherol, gamma-tocotrienol and delta-tocotrienol.

The phytyl-substituted chromanol is typically isolated or purified to homogeneity or near homogeneity. In various embodiments, the chromanol is, prior to admix, purified to at least 80%, preferably at least 90%, more preferably at least 95%, more preferably at least 99% homogeneity. In particular embodiments, the medicament comprises less alpha-T than is present in natural Vitamin E source compositions. In various embodiments, the alpha-T is reduced to less than 50%, preferably less than 20%, more preferably less than 5% of its natural source concentration. In particular embodiments, the pre-admix chromanol/tocopherol is less than 5% alpha-T, more preferably less than 0.5%, more preferably less than 0.05%. The medicament may comprise various mixtures of gamma- and delta-tocopherol and gamma and delta-tocotrienol, including gamma-T+gamma and/or delta tocotrienol, delta-T+gamma and/or delta tocotrienol, and gamma-T+delta-T+gamma and/or delta tocotrienol.

Exploiting the synergy of the components of the medicaments, the $PGE_2$ inhibitor may be provided at a dosage that is suboptimally therapeutic, or to various degrees, subtherapeutic, when administered alone. In various embodiments, the $PGE_2$ inhibitor is provided at or less than 50% of conventional dosages or conventional dosage ranges, preferably at or less than 20% of conventional dosages or ranges. In particular embodiments, the $PGE_2$ inhibitor is an NSAID cyclooxygenase inhibitor, such as an NSAID of Table 1. In other embodiments, the $PGE_2$ inhibitor is a cyclooxygenase-2 (COX) selective inhibitor. In other embodiments, the $PGE_2$ inhibitor is an omega-3 fatty acid cyclooxygenase substrate such as docosahexaenoic acid (DHA) and eicosapentaenoic acid (EPA).

TABLE 1

Suitable NSAID cyclooxygenase inhibitors.

| | | | |
|---|---|---|---|
| Aceclofenac | N-(4-Acetamido-phenyl)-indomethacin amide | Acetylsalicylic acid (aspirin) | 5-Aminosalicylic acid |
| -t-Butyl-alpha-phenylnitrone | Celecoxib | 5-Bromo-2-[4-fluorophenyl]-3-[4-(methylsulfonyl)phenyl]-thiophene (DuP-697) | Diclofenac sodium |
| 5,8,11,14-Eicosatetraynoic acid | 8,11-eicosadiynoic acid | Fenoprofen (Nalfon) | Flurbiprofen |
| S(+)-Ibuprofen | Ibuprofen | Indomethacin heptyl ester solution | Indomethacin |
| Ketorolac Tris salt | Ketoprofen | S(+)-Ketoprofen | Meclofenamate (sodium salt) |
| (S)-6-Methoxy-alpha-methyl-2-naphthalene-acetic acid (Naproxen Sodium Salt) | (S)-6-Methoxy-alpha-methyl-2-naphthal-eneacetic acid (Naproxen) | Meloxicam | Nabumetone |
| Niflumic acid | Nimesulide | N-[2-(Cyclohexyloxy)-4-nitrophenyl]methane-sulfonamide (NS-398) | Nordihydroguaiaretic acid |
| N-(3-Pyridyl)indometh-acinamide | Oxaprozin | Piroxicam | N-(2-Phenylethyl)indo-methacinamide |
| Phenylbutazone | Resveratrol | Rofecoxib | Sulindac sulfide |
| Sulindac sulfone | Tolfenamic acid | Tolmetin | Valdecoxib |

The subject medicament components can be purchased commercially and/or prepared from readily available starting materials using conventional methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

The subject medicament compositions may be administered in conjunction with a carrier, vehicle or excipient suitable for use in pharmaceutical compositions. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition. Such carriers are well known in the pharmaceutical art as are procedures for preparing pharmaceutical compositions.

Depending on the intended route of delivery, the compositions may be administered in one or more dosage form(s) including, without limitation, liquid, solution, suspension, emulsion, tablet, multi-layer tablet, bi-layer tablet, capsule, gelatin capsule, caplet, lozenge, chewable lozenge, bead, powder, granules, dispersible granules, cachets, douche, suppository, cream, topical, inhalant, aerosol inhalant, patch, particle inhalant, implant, depot implant, ingestible, injectable, or infusion. The dosage forms may include a variety of other ingredients, including binders, solvents, bulking agents, plasticizers, etc.

A wide variety of orally administrable compositions may be used. In a particular embodiment, the oral compositions are provided in solid discrete, self-contained dosage units, such as tablets, caplets, lozenges, capsules, gums, etc., which may comprise or be filled with liquid or solid dosages of the recited medicament constituents. A wide variety of dosages may be used, depending on the application and empirical determination; typical dosages range from 1 mg to 1 g, preferably at least 10 mg, more preferably at least 100 mg.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

The above described components are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The dosage forms of the present invention involve the administration of an active therapeutic substance or multiple active therapeutic substances in a single dose during a 24 hour period of time or multiple doses during a 24 hour period of time. The doses may be uneven in that each dose is different from at least one other dose.

The subject compositions may be administered to effect various forms of release, which include, without limitation, immediate release, extended release, controlled release, timed release, sustained release, delayed release, long acting, pulsatile delivery, etc., using well known procedures and techniques available to the ordinary skilled artisan. A description of representative sustained release materials can be found in the incorporated materials in Remington's Pharmaceutical Sciences.

The subject compositions may be formulated for administration by any route, including without limitation, oral, buccal, sublingual, rectal, parenteral, topical, inhalational, including itnranasal, injectable, including subcutaneous, intravenous, intramuscular, etc., topical, including transdermal, etc. The subject compositions are administered in a pharmaceutically (including therapeutically, prophylactically and diagnostically) effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The following formulation examples illustrate representative pharmaceutical compositions of this invention. The present invention, however, is not limited to the following exemplified pharmaceutical formulations:

Formulation 1—Capsules. Acetaminophen and gamma-T are blended with a starch diluent in an approximate 1:3:1 weight ratio. The mixture is filled into 250 mg capsules (approx. 50 mg each of Acetaminophen and 150 mg gamma-T per capsule).

Formulation 2—Capsules. Acetaminophen and delta-T are blended with a starch diluent in an approximate 1:3:1 weight ratio. The mixture is filled into 250 mg capsules (approx. 50 mg each of Acetaminophen and 150 mg delta-T per capsule).

Formulation 3—Capsules. Acetaminophen, gamma-T and gamma-tocotrienol are blended with a starch diluent in an approximate 1:3:3:1 weight ratio. The mixture is filled into 400 mg capsules (approx. 50 mg each of Acetaminophen, 150 mg gamma-T and 150 mg gamma-tocotrienol per capsule).

Formulation 4—Capsules. Aspirin and gamma-T are blended with a starch diluent in an approximate 1:3:1 weight ratio. The mixture is filled into 250 mg capsules (approx. 50 mg each of aspirin and 150 mg gamrna-T per capsule).

Formulation 5—Capsules. Aspirin and delta-T are blended with a starch diluent in an approximate 1:3:1 weight ratio. The mixture is filled into 250 mg capsules (approx. 50 mg each of aspirin and 150 mg delta-T per capsule).

Formulation 6—Capsules. Aspirin, gamma-T and gamma-tocotrienol are blended with a starch diluent in an approximate 1:3:3:1 weight ratio. The mixture is filled into 400 mg capsules (approx. 50 mg each of aspirin, 150 mg gamma-T and 150 mg gamma-tocotrienol per capsule).

Formulation 7—Capsules. Naproxen and gamma-T are blended with a starch diluent in an approximate 1:3:1 weight ratio. The mixture is filled into 250 mg capsules (approx. 50 mg each of naproxen and 150 mg gamma-T per capsule).

Formulation 8—Capsules. Ibuprofen and gamma-T are blended with a starch diluent in an approximate 1:3:1 weight ratio. The mixture is filled into 250 mg capsules (approx. 50 mg each of ibuprofen and 150 mg gamma-T per capsule).

Formulation 9—Capsules. Docosahexaenoic acid (DHA) and gamma-T are blended with a starch diluent in an approximate 1:3:1 weight ratio. The mixture is filled into 250 mg capsules (approx. 50 mg each of DHA and 150 mg gamma-T per capsule).

Formulation 10—Liquid. Acetaminophen (100 mg) and gamma-T are blended (300 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (1189, 50 mg) in water. Sodium benzoate (10 mg), flavor, and color are diluted with water and added with stirring. Sufficient water is then added to produce a total volume of 5 mL.

Formulation 11—Liquid. Aspirin (100 mg) and gamma-T are blended (300 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (1189, 50 mg) in water. Sodium benzoate (10 mg), flavor, and color are diluted with water and added with stirring. Sufficient water is then added to produce a total volume of 5 mL.

Formulation 12—Liquid. Docosahexaenoic acid (DHA) (100 mg) and gamma-T are blended (300 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (1189, 50 mg) in water. Sodium benzoate (10 mg), flavor, and color are diluted with water and added with stirring. Sufficient water is then added to produce a total volume of 5 mL.

Formulation 13—Ointment. Acetaminophen and gamma-T are blended with isopropyl myristate 81 g, fluid paraffin oil 9 g and silica (Aerosil 200, 9 g, Degussa AG, Frankfurt).

Formulation 14—Ointment. Aspirin and gamma-T are blended with isopropyl myristate 81 g, fluid paraffin oil 9 g and silica (Aerosil 200, 9 g, Degussa AG, Frankfurt).

Formulation 15—Ointment. Docosahexaenoic acid (DHA) and gamma-T are blended with isopropyl myristate 81 g, fluid paraffin oil 9 g and silica (Aerosil 200, 9 g, Degussa AG, Frankfurt).

Formulation 16—Non-ionic water-in-oil cream. Acetaminophen and gamma-T are blended with a mixture of emulsified lanolin 39 g alcohols, of waxes and of oils (Anhydrous eucerin, BDF), methyl para-hydroxybenzoate 0.075 g, propyl para-hydroxybenzoate 0.075 g and sterile demineralized 100 g water.

Formulation 17—Non-ionic water-in-oil cream. Aspirin and gamma-T are blended with a mixture of emulsified lanolin 39 g alcohols, of waxes and of oils (Anhydrous eucerin, BDF), methyl para-hydroxybenzoate 0.075 g, propyl para-hydroxybenzoate 0.075 g and sterile demineralized 100 g water.

Formulation 18—Non-ionic water-in-oil cream. Docosahexaenoic acid (DHA) and gamma-T are blended with a mixture of emulsified lanolin 39 g alcohols, of waxes and of oils (Anhydrous eucerin, BDF), methyl para-hydroxybenzoate 0.075 g, propyl para-hydroxybenzoate 0.075 g and sterile demineralized 100 g water.

Formulation 19—Lotion. Acetaminophen and gamma-T are blended with polyethylene glycol (PEG 400) 69 g and 95% Ethanol 30 g.

Formulation 20—Lotion. Aspirin and gamma-T are blended with polyethylene glycol (PEG 400) 69 g and 95% Ethanol 30 g.

Formulation 21—Lotion. Docosahexaenoic acid (DHA) and gamma-T are blended with polyethylene glycol (PEG 400) 69 g and 95% Ethanol 30 g.

Formulation 22—Hydrophobic ointment. Acetaminophen and gamma-T are blended with isopropyl myristate 36 g, silicone oil (Rhodorsil 36.400 g 47 V 300, Rhone-Poulenc), beeswax 13 g and silicone oil (Abil 300 100 g cst, Goldschmidt).

Formulation 23—Hydrophobic ointment. Aspirin and gamma-T are blended with isopropyl myristate 36 g, silicone oil (Rhodorsil 36.400 g 47 V 300, Rhone-Poulenc), beeswax 13 g and silicone oil (Abil 300 100 g cst, Goldschmidt).

Formulation 24—Hydrophobic ointment. Docosahexaenoic acid (DHA) and gamma-T are blended with isopropyl myristate 36 g, silicone oil (Rhodorsil 36.400 g 47 V 300, Rhone-Poulenc), beeswax 13 g and silicone oil (Abil 300 100 g cst, Goldschmidt).

The invention also provides methods of inhibiting inflammation by administering to a patient a subject medicament. In a particular embodiment of this aspect, the invention provides a method for treating a patient with an inflammatory disease which method comprises administering to said patient a pharmaceutical composition comprising a pharmaceutically acceptable carrier and an effective inflammatory disease-treating amount of a subject medicament. Additionally, this invention is directed to a method for preventing the onset of an inflammatory disease in a patient at risk for developing the inflammatory disease which method comprises administering to said patient a pharmaceutical composition comprising a pharmaceutically acceptable carrier and an effective inflammatory disease-preventing amount of a subject medicament. In preferred embodiments of this invention, the inflammatory disease treated and/or prevented in the above methods is rheumatoid arthritis, septic shock, erythema nodosum leprosy, septicemia, uveitis and the like.

This aspect of the invention may be implemented by a first diagnostic step, e.g. determining that the patient is suffering from, subject to, or predisposed to a target disease or condition followed by prescribing and/or administering to the patient a subject medicament, optionally followed by an evaluation/confirmation/prognosis step, e.g. determining an effect of the treatment, such as an amelioration of symptoms of a targeted disease or condition or an indicator thereof.

The following empirical and experimental examples are offered to illustrate this invention and are not to be construed in any way as limiting the scope of this invention.

EMPIRICAL EXAMPLES

I. Oral Formulations 1-12 (Supra) Demonstrate Intestinal Anti-inflammatory Efficacy in vivo For this experimental protocol, we adapted methods originally described by Galvez J, Aliment Pharmacol Ther 2001 December; 15(12):2027-39, to assess the anti-inflammatory activity of the formulations in the chronic stages of trinitrobenzenesulphonic acid-induced rat colitis. In our methods, rats are rendered colitic by a single colonic instillation of 30 mg of the hapten trinitrobenzenesulphonic acid dissolved in 0.25 mL of 50% ethanol. A group of colitic animals is given one of formulations 1-24 (supra) orally at doses of 25 mg/kg daily. Animals are sacrificed every week for 4 weeks. Colonic damage is evaluated macroscopically and microscopically. Different biochemical markers of colonic inflammation are also assayed, including myeloperoxidase activity, leukotriene B4 and interleukin-1beta synthesis, glutathione and malonyl-dialdehyde levels and nitric oxide synthase activity.

The administration of our formulations facilitates tissue recovery during the 4 weeks following colonic insult with trinitrobenzenesulphonic acid, as demonstrated macroscopically and microscopically, as well as biochemically by a reduction in myeloperoxidase activity. The intestinal anti-inflammatory effect is accompanied by a significant reduction in colonic leukotriene B4 and interleukin-1beta levels, improvement in colonic oxidative stress and inhibition of colonic nitric oxide synthase activity. We conclude that our oral formulations exert a beneficial anti-inflammatory effect in the chronic phase of trinitrobenzenesulphonic acid-induced rat colitis through the down-regulation of some of the mediators involved in the intestinal inflammatory response, including free radicals, cytokines, leukotriene B4 and nitric oxide.

II. Oral Formulations 1-12 (Supra) Reduce Carrageenan-induced Inflammation in the Air-pouch Animal Model.

For this experimental protocol, we adapted the methods recited in the Experimental Example reported below. As cited below, carrageenan-induced inflammation in the air-pouch model was performed and evaluated substantially as previously described (14). Formulations were administered as described below, wherein the recited tocopherol was dissolved in tocopherol-stripped corn oil, and continuously administrated by gavage for three days before the induction of inflammation. The $PGE_2$ component of the formulation was empirically varied and adjusted to provide a minimized synergistic concentration. For example, aspirin formulations were adjusted to 50 or 100 mg/Kg with gamma-T at 30 mg/Kg. In controls evaluating the effects of aspim or gamma-T alone, we increased the aspririn dosage to 150 mg/Kg and gamma-T to 30 mg/kg, respectively. These studies demostrate that our formulations provide more potent effects on inhibition of PGE2 and LTB4, TNF-a etc than either alone.

III. Topical Formulations 13-24 (Supra) Demonstrate Topical Anti-inflammatory Efficacy In Vivo For this experimental protocol, we adapted the methods of Parneix-Spake A, et al. (J Dermatolog Treat 2001 December; 12(4): 191-7) to compare the healing properties of our topical formulations 13-24 (0.05% cream) with their emollient base, hydrocortisone 1% cream and with no treatment, in a single-center, double-blind, intra-individual, comparative study involving 18 volunteers with nickel-induced contact dermatitis. Following a positive patch test to nickel, sub-therapeutic amounts (10 micro 1=3 mg cm(−2)) of each of the treatments are applied twice daily for seven days to each of the four test sites.

In terms of the primary endpoint, a physician's global assessment after 7 days of treatment, each of formulations 13-24 (0.05% cream) shows a significantly better response than hydrocortisone (HC) 1% cream or no treatment. Our 0.05% formulation creams also show a better response than their emollient base. In terms of moisturizing effects, there was no difference in transepidermal water loss (TEWL) between 0.05% formulation creams and their emollient base. In terms of skin blanching activity, the steroid-based creams achieve lower colorimetric values than the emollient base cream. Results from experimentally induced skin inflammation indicate that our 0.05% formulation creams have both more effective anti-inflammatory activity and better moisturizing properties than hydrocortisone 1% cream.

EXPERIMENTAL EXAMPLES

Carrageenan-induced inflammation in the air-pouch model was performed and evaluated substantially as previously described (14). Alpha-T and gamma-T were measured in plasma and exudate as previously described (12). Gamma-CEHC was quantified essentially as previously described (13).

For the measurement of $PGE_2$, $LTB_4$ and 8-isoprostane, the exudate fluid was mixed vigorously with 2 mL methanol to precipitate proteins, and with 5 mL hexane to remove lipids. Following a brief centrifugation and aspiration of the hexane layer, the methanol layer was removed and evaporated under $N_2$. $PGE_2$, $LTB_4$ and 8-isoprostane were measured using the corresponding ELISA kits from Cayman Chemicals (Ann Arbor, Mich.). TNF-a and lactate dehydrogenase (LDH) in the exudate were measured directly using an ELISA kit from R&D (Minneapolis, Minn.) and an analytical kit from Roche (Indianapolis, Ind.), respectively.

The total amount of nitrate and nitrite in the exudate was measured using the Model 280 nitric oxide analyzer (NOA™) (Sievers Instruments, Inc.; Boulder, Colo.). Nitrite and nitrate in the exudate were reduced by vanadium (III) to nitric oxide, which then was measured by a red-sensitive photomultiplier tube after being converted by ozone to chemiluminescent reactive nitrogen dioxide. Nitrite and nitrate were quantified based on a standard curve from nitrate that was established under the identical conditions.

Administration of gamma-T and its major metabolite, gamma-CEHC, but not alpha-T, significantly inhibits pro-inflammatory eicosanoids at the site of inflammation. Carrageenan-induced inflammation in the air-pouch model is commonly used to evaluate the pharmaceutical potency of anti-inflammatory drugs (14). In this model, an injection of air into the intrascapular area resulted in the formation of a connective tissue cavity mainly lined with macrophages and fibroblasts (11, 15). These cells play a key role in the inflammatory response (11, 14, 15). A single injection of carrageenan caused a potent localized inflammation, as indicated by a marked increase in white cell infiltration, eicosanoid formation and tissue damages (11). To study the effect of gamma-CEHC on eicosanoid synthesis and neutrophil infiltration, it (1 mg/ml, 2 ml in PBS) was injected directly into the air pouch right before the injection of carrageenan. Since the retention of gamma-CEHC is relatively short (16), its effect was evaluated at 6 h after the induction of inflammation. Administration of gamma-CEHC significantly reduced $PGE_2$ (~29%, $P<0.05$) in the pouch, which is consistent with our previous observations in vitro (10). At this dose, gamma-CEHC also inhibited $LTB_4$ and neutrophil infiltration, though non-significantly.

To test the effects of tocopherols, alpha-T or gamma-T, dissolved in tocopherol-stripped corn oil, was continuously administrated by gavage for three days before the induction of inflammation. Effects were evaluated at 20 h after carrageenan injection, when cell infiltration had reached a maximum in the pouch. At a dose of 33 mg/kg, gamma-T, but not alpha-T, significantly reduced the pro-inflammatory $PGE_2$ (46%, $P<0.05$) and $LTB_4$ (70%, $P<0.05$), a potent chemotactic eicosanoid produced by the 5-lipoxygenase in neutrophils. At a higher dose, i.e. 100 mg/kg, gamma-T showed an inhibitory potency against $PGE_2$ (51%, $P<0.05$) and $LTB_4$ similar to the lower dose. Despite the inhibitory effects on $PGE_2$ and $LTB_4$, gamma-T did not affect neutrophil infiltration.

Gamma-T reduced TNF-a and total nitrite and nitrate at the higher dose of 100 mg/kg. In addition to the eicosanoids, we have investigated the effects of gamma-T on TNF-a, an important inflammation mediator, and total nitrite and nitrate, an index of the generation of reactive nitrogen oxides. At the lower dose of 33 mg/kg, gamma-T non-significantly inhibited TNF-a (~51%, $P=0.29$), but had no effect on total nitrate and nitrite. At the higher dose of 100 mg/kg, gamma-T reduced TNF-a (65%, $P=0.069$) and total nitrite and nitrate (40%, $P=0.1$). Administration of gamma-T attenuates the partial loss of food consumption induced by inflammation, and inhibits inflammation-mediated lipid peroxidation and cytotoxicity. The effect of gamma-T and alpha-T on inflammation-induced lipid peroxidation and inflammation-site tissue damage was assayed by the 8-isoprostane level (17) and by the release of lactate dehydrogenase (LDH), respectively (11). Carrageenan-induced inflammation resulted in a marked increase in 8-isoprostane and LDH in the pouch. In contrast to alpha-T (33 mg/kg), gamma-T at the dose of 33 or 100 mg/kg significantly reduced 8-isoprostane (for both doses, ~57%, $P<0.05$) in the pouch gamma-T, at the higher dose of 100 mg/kg, lowered LDH (30%, $P=0.067$), a marker of cytotoxicity and tissue damage. In addition, carrageenan-induced inflammation resulted in a marked reduction in food consumption (~40%, $P<0.01$), which is likely caused by the discomfort associated with inflammation. Administration of gamma-T at 100 mg/kg significantly attenuated (30%, $P<0.03$) the loss of food consumption, while a smaller, non-significant, effect was observed at the lower dose of 33 mg/kg (20%, $P=0.2$).

Plasma and exudate concentrations of alpha-T, gamma-T and gamma-CEHC. To evaluate the relative bio-availability of the administered compounds, we measured plasma and exudate concentrations of gamma-T and alpha-T as well as plasma gamma-CEHC. Administration of alpha-T or gamma-T led to the significant increases in both tocopherols in the plasma and exudate, while their relative increase in the exudate is more than that in the plasma. Thus, gamma-T-administrated (33 or 100 mg/kg) rats had nearly 10- or 20-fold elevation of gamma-T in exudates fluid, in contrast to 3- or 5-fold increase in the plasma, as compared with corn-oil fed controls. With alpha-T, a similar trend also was observed. In gamma-T-administrated rats (33 or 100 mg/kg), the ratio of gamma-T to alpha-T in the exudate (~0.3 or 0.7) is higher than that in the plasma (~0.15), consistent with the idea that tissues may have a higher gamma-T partition than does plasma (18). gamma-T administration did not significantly affect alpha-T, but alpha-T caused significant decreases of gamma-T both in the plasma (~55%, $P<0.05$) and exudate (40%, $P<0.05$). gamma-CEHC, the major metabolite of gamma-T, increased in response to gamma-T supplementation. Nano-molar concentrations of gamma-CEHC were found in the plasma, a level less than 10% that of plasma gamma-T. gamma-T administration caused a 2.5-4 fold elevation of gamma-CEHC in the plasma.

Carrageenan-induced inflammation in the rat air pouch model mimics the pathological process occurring in the joint diseases such as arthritis; the connective tissues formed along the air pouch are similar to those found in chronic joint diseases (11, 15). Carrageenan-induced inflammation and chronic joint diseases also share other features including markedly elevated $PGE_2$, neutrophil infiltration, cytokine formation and tissue damage (11). Studies have established that in this model, COX-2, which is quickly induced in the lining macrophages and fibroblasts, is the primary enzyme responsible for the elevation of $PGE_2$ (14). Thus, various COX-2 inhibitors have been shown to inhibit the formation of $PGE_2$ in the pouch (14). We recently found that the major form of vitamin E in the diet, gamma-T, and its metabolite, but not alpha-T, the major form in supplements, effectively inhibited COX-2 activity in lipopolysachariade-activated macrophages and interlukin-1b-treated epithelial cells (10). In line with this in vitro observation, the present study shows that in the carrageenan air pouch model, gamma-T (33 or 100 mg/kg), in contrast to alpha-T (33 mg/kg), significantly lowered $PGE_2$ elevation at the site of inflammation. Local delivery of gamma-CEHC into the air pouch also led to a significant inhibition of $PGE_2$. These results therefore demonstrate that gamma-T and gamma-CEHC show in vivo anti-inflammatory properties that appear to be similar to those of NSAIDs. In addition, gamma-T but not alpha-T significantly inhibits $LTB_4$, a potent chemotactic agent that is synthesized by 5-lipoxygenase of neutrophils (8).

In addition to the inhibitory effects on the pro-inflammatory eicosanoids, gamma-T administration reduced inflammation-mediated damage as shown by its reduction of lipid peroxidation and LDH activity. gamma-T attenuated the marked loss of food consumption that is likely caused by the inflammation-associated discomfort. Because $PGE_2$ is known to play a key role in causing pain and fever, a reduction of this eicosanoid may in part explain gamma-T's effect on the food consumption. In addition, other unique properties of gamma-T may also contribute to the observed beneficial effects (18). Because of the unsubstituted 5-position, compared with alpha-T, gamma-T is capable of trapping reactive nitrogen oxide to form a stable nitrated adduct (19). Thus, gamma-T is better than alpha-T in the protection of peroxynitrite-induced lipid peroxidation (19) and enzyme inactivation (20). We recently found that in the zymosan-induced inflammation model, gamma-T supplementation consistently inhibited protein nitration and ascorbate oxidation (12).

At 100 mg/kg but not 33 mg/kg, gamma-T lowers the accumulation of total nitrate and nitrite. Although some studies show that reactive nitric oxide stimulates $PGE_2$ formation (21, 22), in the current model, however, these two events appear to be independent because gamma-T decreases $PGE_2$ at both doses. In LPS-stimulated macrophages, we previously found that gamma-T moderately inhibits nitrite accumulation via a moderate inhibition of the induction of inducible nitric oxide synthase (10). It is possible that the currently observed reduction of total nitrate and nitrite is caused by gamma-T's suppression of this enzyme. Alternatively, gamma-T's capability of trapping reactive nitrogen oxides may also result in lowered levels of total nitrate and nitrite. However, we did not observe an apparent increase in 5-nitro-gamma-tocopherol in the exudate fluid. Nevertheless, this possibility cannot be ruled out due to the lack of measuring 5-nitro-gamma-CEHC, a putative breakdown product of 5-nitro-gamma-tocopherol (18).

Gamma-T can decrease TNF-a, a key proinflammatory cytokine known to activate macrophages and provoke the inflammatory response (23). Studies have shown that inhibition of TNF-a provides beneficial effects on inflammatory diseases (24). The utilization of antibody against TNF-a has been proven to be an effective therapy for inflammatory disease (25).

Although gamma-T significantly inhibits the pro-inflammatory eicosanoids, it has no effect on the neutrophil infiltration. It has been shown that in the carrageenan air-pouch model, there is no casual correlation between the inhibition of $PGE_2$ and neutrophil infiltration (11). For example, aspirin, at doses of 100-150 mg/kg, caused 50-70% reduction of $PGE_2$, but yet it did not affect neutrophil infiltration (26). Although at higher doses, i.e. >200-300 mg/kg, aspirin inhibits cell infiltration, the mechanisms may include the inhibition of NFkB signal transduction (27) or the activation of adenosine formation (28).

The relatively high bio-availability of gamma-T contributes to its in vivo inhibition of eicosanoids in the pouch. gamma-T administration resulted in a more pronounced elevation of this tocopherol in the exudate than that in the plasma. When gamma-T showed significant inhibitory effects on $PGE_2$ at 20-h after the injection of carrageenan, its concentration in the collected exudate was estimated to be 93.3 (33 mg/kg) to 193 nmol/gprotein (100 mg/kg), corresponding to ~10 to 20 mM, which is comparable to the apparent $IC_{50}$ (~5-10 mM) estimated in the cell culture (10). An increase in gamma-T administration from 33 to 100 mg/kg did not significantly improve the inhibitory potency, probably due to the saturation effect. Although gamma-CEHC, when applied directly into the pouch, significantly inhibited $PGE_2$, the effect of gamma-T cannot be attributed to this metabolite. This is because the concentration of gamma-CEHC is in the nanomolar range, which is much lower than the estimated $IC_{50}$ (30-40 mM) for g-CEHC to inhibit COX-2 activity (10). Though as much as 50% of gamma-T may be converted to gamma-CEHC (29), this metabolite is not likely to be accumulated in the plasma or tissues (except the kidney) because of its short retention time (16).

In the present study, although administration of alpha-T (33 mg/kg) led to an approximately 2-fold increased level in the plasma and exudate, alpha-T did not show any significant effects with respect to the generation of eicosanoids and 8-isoprostane, in line with our in vitro observations (10). It may be also relevant that alpha-T has a high baseline in tissues as a result of the high content of alpha-T in the diet. However, administration of the same dose of gamma-T did show significant effects. This observation indicates that gamma-T possesses unique properties that are not shared alpha-T (18). Because alpha-T is preferentially retained by the body and is the strongest antioxidant in the vitamin E family, supplementation of both gamma-T and alpha-T (especially when alpha-T is relatively low) may result in better outcomes.

Not only does gamma-T reduce $PGE_2$, but it also inhibits lipoxygenase-catalyzed synthesis of $LTB_4$ as well as decreases TNF-a, an activity most NSAIDs do not have (26). These findings indicate a potentially superior pharmaceutical use of gamma-T compared with traditional NSAIDs. Gamma-T may be useful in cancer prevention. It is known that COX-2 and $PGE_2$ are elevated in inflammation-associated diseases including cancer (30). Frequent intake of NSAIDs such as aspirin is known to reduce the risk of certain cancers (31, 32). Recently, Helzlsouer et al. (33) reported that in a nested case-control study, men in the highest quintile of plasma gamma-T levels had a 5-fold reduction in the risk of prostate cancer compared to those in the lowest quintile. We recently found that gamma-T but not alpha-T showed anti-proliferative effects on prostate and lung cancer cell lines, but had no effect on normal epithelial cells. The anti-inflammatory effects of gamma-T may be beneficial in cardiovascular disease, another inflammation-associated disorder (34). Several studies (35, 36) reported that plasma concentrations of gamma-T, but not alpha-T, are inversely associated with the incidence of coronary heart diseases.

This experimental example shows that gamma-T inhibits the pro-inflammatory eicosanoids, suppresses pro-inflammatory cytokines and attenuates inflammation-caused damage in an in vivo rat inflammation model.

PARENTHETICAL REFERENCES

1. Balkwill, F., and Mantovani, A. (2001) *Lancet* 357, 539-545.
2. Libby, P., Ridker, P. M., and Maseri, A. (2002) *Circulation* 105, 1135-1143.
3. McGeer, P. L., and McGeer, E. G. (2001). *Neurobiol Aging* 22, 799-809.
4. Vane, J. R. (1976). *Adv Prostaglandin Thromboxane Res* 2, 791-801
5. Samad, T. A., et al. (2001). *Nature* 410, 471-475.
6. Williams, J. A., and Shacter, E. (1997) 2. *J Biol Chem* 272, 25693-25699
7. Vane, J. R., and Botting, R. M. (1998). *Int J Tissue React* 20, 3-15
8. Yokomizo, T., Izumi, T., and Shimizu, T. (2001) *Arch Biochem Biophys* 385, 231-241.
9. Wynne, H. A., and Campbell, M. (1993) *Pharmacoeconomics* 3, 107-123.

10. Jiang, Q., Elson-Schwab, I., Courtemanche, C., and Ames, B. N. (2000) *Proc Natl Acad Sci USA* 97, 11494-11499.
11. Sedgwick, A. D., and Lees, P. (1986) *Agents Actions* 18, 429-438.
12. Jiang, Q., Lykkesffeldt, J., Shigenaga, M. K., Shigeno, E. T., Christen, S., and Ames, B. N. (2002) Gamma-tocopherol inhibits protein nitration and ascorbate oxidation in rats with inflammation. *Free Rad Biol Med* 33, in press
13. Stahl, W., et al. (1999) *Anal Biochem* 275, 254-259
14. Masferrer, J. L., et al. (1994) *Proc Natl Acad Sci USA* 91, 3228-3232.
15. Sedgwick, A. D., et al. (1983) *J Pathol* 141, 483-495.
16. Murray, E. D., Jr., et al. (1997) *J Pharmacol Exp Ther* 282, 657-662.
17. Morrow, J. D. (2000) *Drug Metab Rev* 32, 377-385.
18. Jiang, Q., Christen, S., Shigenaga, M. K., and Ames, B. N. (2001) *Am J Clin Nutr* 74, 714-722.
19. Christen, S., Woodall, A. A., Shigenaga, M. K., Southwell-Keely, P. T., Duncan, M. W., and Ames, B. N. (1997) *Proc Natl Acad Sci USA* 94, 3217-3222.
20. Williamson, K. S., et al. (2002) *Nitric Oxide* 6, 221-227.
21. Beharka, A. A., et al. (2002) *Free Radic Biol Med* 32, 503-511
22. Landino, L. M., et al. (1996). *Proc Natl Acad Sci USA* 93, 15069-15074
23. Belardelli, F. (1995) *Apmis* 103, 161-179.
24. Criscione, L. G., and St Clair, E. W. (2002) *Curr Opin Rheumatol* 14, 204-211.
25. Lorenz, H. M., and Kalden, J. R. (2002) *Arthritis Res* 4, S17-24.
26. Kirchner, T., et al. (1997) *J Pharmacol Exp Ther* 282, 1094-1101.
27. Yin, M. J., Yamamoto, Y., and Gaynor, R. B. (1998) *Nature* 396, 77-80.
28. Cronstein, B. N., et al. (1999) *Proc Natl Acad Sci USA* 96, 6377-6381.
29. Swanson, J. E., et al. (1999) *J Lipid Res* 40, 665-671.
30. Marnett, L. J. (1992) *Cancer Res* 52, 5575-5589.
31. Smalley, W. E., and DuBois, R. N. (1997) *Adv Pharmacol* 39, 1-20
32. Thun, M. J., et al. (1993) *Cancer Res* 53, 1322-1327
33. Helzlsouer, K. J., et al. (2000) *J Natl Cancer Inst* 92, 2018-2023.
34. Plutzky, J. (2001) *Am J Cardiol* 88, 10K-15K.
35. Kristenson, M., et al. (1997) *Bmj* 314, 629-633
36. Ohrvall, M., Sundlof, G., and Vessby, B. (1996) *J Intern Med* 239, 111-117

The foregoing descriptions of particular embodiments and examples are offered by way of illustration and not by way of limitation. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

All publications and patent applications cited in this specification and all references cited therein are herein incorporated by reference as if each individual publication or patent application or reference were specifically and individually indicated to be incorporated by reference. Any material accompanying this application on compact disc or other recorded medium is incorporated by reference.

What is claimed is:

1. A method of inhibiting proliferation of human prostate epithelial cancer cells or human lung epithelial cancer cells in a person, the method comprising administering to the person in unit dosage form a medicament consisting of 150 mg gamma-tocopherol, 150 mg gamma-tocotrienol, 50 mg acetaminophen, and one or more carrier, vehicle or excipient suitable for use in pharmaceutical compositions.

2. The method of claim 1 wherein the cells are the human prostate epithelial cancer cells and the medicament is administered orally.

3. The method of claim 1 wherein the cells are the human lung epithelial cancer cells and the medicament is administered as an inhalant.

4. A method of inhibiting proliferation of human prostate epithelial cancer cells or human lung epithelial cancer cells in a person, the method comprising administering to the person in unit dosage form a medicament consisting of 150 mg gamma-tocopherol, 150 mg gamma-tocotrienol, 50 mg aspirin, and one or more carrier, vehicle or excipient suitable for use in pharmaceutical compositions.

5. The method of claim 4 wherein the cells are the human prostate epithelial cancer cells and the medicament is administered orally.

6. The method of claim 4 wherein the cells are the human lung epithelial cancer cells and the medicament is administered as an inhalant.

* * * * *

UNITED STATES PATENT AND TRADEMARK OFFICE
CERTIFICATE OF CORRECTION

| | | |
|---|---|---|
| PATENT NO. | : 7,964,587 B2 | Page 1 of 1 |
| APPLICATION NO. | : 11/159917 | |
| DATED | : June 21, 2011 | |
| INVENTOR(S) | : Bruce N. Ames et al. | |

It is certified that error appears in the above-identified patent and that said Letters Patent is hereby corrected as shown below:

The government support paragraph at col. 1, lines 6-9 should read as follows:

This invention was made with US Government support under Public Health Service Grant No. ES001896. The government has certain rights in this invention.

Signed and Sealed this
Ninth Day of April, 2013

Teresa Stanek Rea
*Acting Director of the United States Patent and Trademark Office*